(12) United States Patent
Aamodt et al.

(10) Patent No.: US 7,968,226 B2
(45) Date of Patent: *Jun. 28, 2011

(54) CONTOURED BATTERY FOR IMPLANTABLE MEDICAL DEVICES AND METHOD OF MANUFACTURE

(75) Inventors: Paul B. Aamodt, Richfield, MN (US); Franise D. Bartley, Maple Grove, MN (US); Steve M. Bruesehoff, Waconia, MN (US); Kurt J. Casby, Grant, MN (US); David P. Haas, Brooklyn Park, MN (US); Karl E. Hokanson, Coon Rapids, MN (US); Thomas M. Nutzman, Andover, MN (US); Andrew J. Ries, Uno Lakes, MN (US); Scott J. Robinson, Forest Lake, MN (US); Randy S. Roles, Crystal, MN (US); Sonja K. Somdahl, Minneapolis, MN (US); Walter C. Sunderland, Eagan, MN (US); Jason T. Papenfuss, Saint Paul, MN (US); William J. Farrell, Arden Hills, MN (US); Kimberly A. Chaffin, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1214 days.

This patent is subject to a terminal disclaimer.

(21) Appl. No.: 11/565,306

(22) Filed: Nov. 30, 2006

(65) Prior Publication Data
US 2007/0099077 A1 May 3, 2007

Related U.S. Application Data

(63) Continuation of application No. 10/260,625, filed on Sep. 30, 2002, now abandoned.

(51) Int. Cl.
*H01M 2/04* (2006.01)
*H01M 2/06* (2006.01)
*H01M 2/08* (2006.01)

(52) U.S. Cl. ........ 429/169; 429/175; 429/176; 429/185; 29/623.1

(58) Field of Classification Search .......... 429/167–169, 429/171, 174–176, 185; 29/623.1
See application file for complete search history.

(56) References Cited

U.S. PATENT DOCUMENTS
3,957,056 A 5/1976 Comben
(Continued)

OTHER PUBLICATIONS

Hawley's Condensed Chemical Dictionary, 11th edition, p. 1146. 1987 (no month).*

*Primary Examiner* — Tracy Dove
(74) *Attorney, Agent, or Firm* — Carol F. Barry

(57) ABSTRACT

A battery having an electrode assembly located in a housing that efficiently utilizes the space available in many implantable medical devices is disclosed. The battery housing provides a cover and a shallow case a preferably planar, major bottom portion, an open top to receive the cover opposing the bottom portion, and a plurality of sides being radiused at intersections with each other and with the bottom to allow for the close abutting of other components located within the implantable device while also providing for efficient location of the battery within an arcuate edge of the device. The cover and the shallow case being substantially hermetically sealed by a laser weld technique and an insulator member disposed within the case to provide a barrier to incident laser radiation so that during welding radiation does not impinge upon radiation sensitive component(s) disposed within the case.

29 Claims, 14 Drawing Sheets

U.S. PATENT DOCUMENTS

| | | |
|---|---|---|
| 4,243,042 A | 1/1981 | Ware |
| 5,103,818 A | 4/1992 | Maston |
| 5,456,698 A | 10/1995 | Byland |
| 5,458,997 A | 10/1995 | Crespi |
| 5,470,341 A | 11/1995 | Kuehn |
| 5,486,215 A | 1/1996 | Kelm |
| 5,500,026 A | 3/1996 | Heller |
| 5,549,717 A | 8/1996 | Takeuchi |
| 5,549,985 A | 8/1996 | Heller |
| 5,616,429 A | 4/1997 | Klementowski |
| 6,004,692 A | 12/1999 | Muffoletto |
| 6,040,082 A | 3/2000 | Haas |
| 6,399,243 B1 | 6/2002 | Kaplan |
| 6,579,640 B1 | 6/2003 | Nagase |
| 6,610,443 B2 | 8/2003 | Paulot |
| 6,613,474 B2 | 9/2003 | Frustaci |
| 6,776,300 B2 | 8/2004 | Walsh |
| 2004/0062986 A1 | 4/2004 | Aamodt |

* cited by examiner

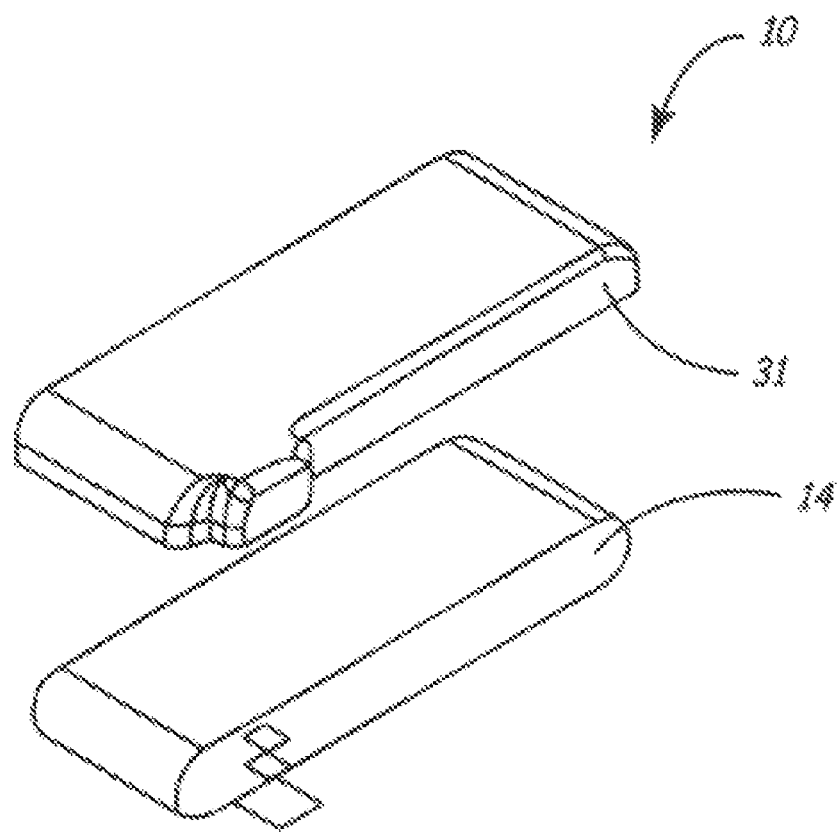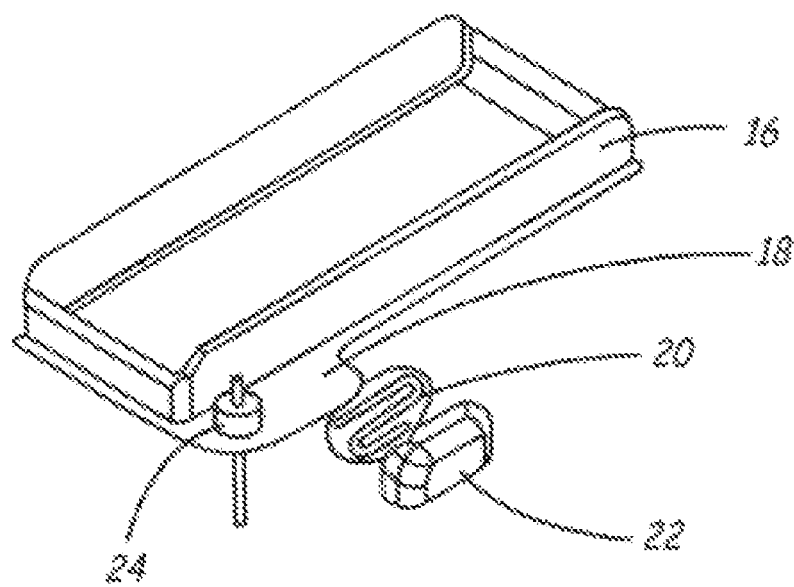
FIG. 1

CONTOURED BATTERY FOR IMPLANTABLE MEDICAL DEVICES AND METHOD OF MANUFACTURE

CROSS-REFERENCES TO RELATED APPLICATIONS

This application is a continuation of application Ser. No. 10/260,625, filed on Sep. 30, 2002 now abandoned, entitled CONTOURED BATTERY FOR IMPLANTABLE MEDICAL DEVICES AND METHOD OF MANUFACTURE.

FIELD OF THE INVENTION

The present invention relates to the field of batteries for implantable medical devices. More particularly, the present invention relates to volumetrically efficient batteries for implantable medical devices.

BACKGROUND OF THE INVENTION

Implantable medical devices are used to treat patients suffering from a variety of conditions. Examples of implantable medical devices are implantable pacemakers and implantable cardioverter-defibrillators (ICDs), which are electronic medical devices that monitor the electrical activity of the heart and provide electrical stimulation to one or more of the heart chambers, when necessary. For example, a pacemaker senses an arrhythmia, i.e., a disturbance in heart rhythm, and provides appropriate electrical stimulation pulses, at a controlled rate, to selected chambers of the heart in order to correct the arrhythmia and restore the proper heart rhythm. The types of arrhythmias that may be detected and corrected by pacemakers include bradycardias, which are unusually slow heart rates, and certain tachycardias, which are unusually fast heart rates.

Implantable cardioverter-defibrillators (ICDs) also detect arrhythmias and provide appropriate electrical stimulation pulses to selected chambers of the heart to correct the abnormal heart rate. In contrast to pacemakers, however, an ICD can also provide pulses that are much stronger and less frequent. This is because ICDs are generally designed to correct fibrillations, which is a rapid, unsynchronized quivering of one or more heart chambers, and severe tachycardias, where the heartbeats are very fast but coordinated. To correct such arrhythmias, an ICD delivers a low-, moderate-, or high-energy shock to the heart.

Pacemakers and implantable defibrillator devices are preferably designed with shapes that are easily accepted by the patient's body while minimizing patient discomfort. As a result, the corners and edges of the devices are typically designed with generous radii to present a package having smoothly contoured surfaces. It is also desirable to minimize the volume occupied by the devices as well as their mass to further limit patient discomfort. As a result, the devices continue to become thinner, smaller, and lighter.

In order to perform their pacing and/or cardioverting-defibrillating functions, pacemakers and ICDs must have an energy source, e.g., at least one battery. Known high current power sources used in implantable defibrillator devices employ deep, prismatic, six-sided rectangular solid shapes in packaging of the electrode assemblies. Examples of such deep package shapes can be found in, e.g., U.S. Pat. No. 5,486,215 (Kelm et al.) and U.S. Pat. No. 6,040,082 (Haas et. al.). While these prismatic cases have proven effective for housing and electrically insulating the electrode assemblies, there are volumetric inefficiencies associated with deep prismatic cases.

One volumetric problem associated with deep prismatic cases is the excess volumetric size of the implantable medical device caused by placing these prismatic batteries within the contoured implantable medical device. As stated above, implantable medical devices are preferably designed with shapes that are easily accepted by the patient's body and which also minimize patient discomfort. Therefore, the corners and edges of the devices are typically designed with generous radii to present a package having smoothly contoured surfaces. When the deep prismatic battery is placed within the contoured implantable device, the contours of these devices do not necessarily correspond and thus the volume occupied within the implantable device cannot be optimally minimized to further effectuate patient comfort.

Another volumetric problem associated with deep prismatic cases is the excess volume within the headspace. In a typical implantable device battery the headspace houses the electrode connector tabs, feedthrough pin, insulators, and various other connection components. In typical deep battery cases, the battery case has a prismatic top and then descends downward with possibly curved sides to a bottom. Thus while deep cases could provide for slightly contoured sides it could not provide for contours all throughout the battery case. Thus as shown in FIG. 13, the battery case would have to extend above the electrode assembly to accommodate the electrode connector tabs, feedthrough pin, etc. This is volumetrically inefficient since all that technically needs to extend from the top of the electrode assembly is the electrode connector tabs and the feedthrough pin. This inefficiency is due to manufacturing limitations, which make it difficult to create several curved surfaces in deep battery cases.

Although the use of curved battery cases in implantable devices is known, they are typically found in devices requiring only low current discharge such as pacemakers as described in U.S. Pat. No. 5,549,985 and U.S. Pat. No. 5,500,026. However, these batteries used thin, flat-layered electrodes that do not package efficiently within curved cases, thus contributing to volumetric inefficiencies. Batteries with curved cases have been used in connection with the high current batteries required for, e.g., implantable defibrillator devices. However, as discussed above, the curvature of these battery cases is limited due to manufacturing limitations associated with deep cases.

For the foregoing reasons, there is a need for a contoured, low profile battery for implantable medical devices, which allows for shape flexibility in the design of the battery to match the contours of an implantable device and fit within the available device space thus providing for a reduction in the volume of the implantable device.

BRIEF SUMMARY OF THE INVENTION

The present invention comprises various embodiments which provide solutions to one or more problems existing in the prior art respecting efficient battery case design for implantable medical devices. Among the problems in the prior art is the lack of a battery case design for use with electrode assemblies that can be: (1) efficiently packaged within an arcuate edge of the implantable device housings, (2) substantially reduces the amount of volume utilized within the implantable medical device and (3) provides flexibility in the placement of the feedthrough pin.

Accordingly, it is an object of the invention to provide a battery having a high surface area electrode assembly housed in a case that efficiently utilizes the space available within many implantable medical devices.

Battery housings in embodiments of the invention may include one or more of the following features: (a) a cover, (b) a shallow case having a (preferably) planar bottom portion, an open top to receive the cover; and at least two sides being radiused at intersections with the bottom, (c) a feedthrough assembly providing electrical communication between at least one electrode and implantable medical device circuitry, (d) a coupling providing electrical communication between the feedthrough assembly and the at least one electrode, (e) an insulator adjacent to the cover providing a barrier between an electrode assembly and the cover, (f) an insulator adjacent to the case providing a barrier between the electrode assembly and the case, and (g) a headspace portion extending from a portion of one of the sides.

Batteries in one or more embodiments of the present invention may include one or more of the following features: (a) an electrode assembly including an anode and a cathode, (b) an electrolyte, (c) a battery housing enclosing the electrode assembly and within which the electrode assembly and the electrolyte are disposed, the housing comprising a cover, a shallow case having a (preferably) planar bottom portion, an open top to receive the cover; and a plurality of sides being radiused at intersections with each other and with the bottom, (d) a headspace region extending from a portion of one of the plurality of sides, (e) a feedthrough assembly providing electrical communication between at least one electrode and implantable medical device circuitry, (f) a coupling providing electrical communication between the feedthrough assembly and the at least one electrode, (g) an insulator adjacent to the cover providing a barrier between an electrode assembly and the cover, (h) and an insulator adjacent to the case providing a barrier between the electrode assembly and the case.

Implantable defibrillator devices in one or more embodiments of the present invention may include one or more of the following features: (a) a device housing comprising at least one arcuate edge, (b) a capacitor disposed within the device housing, (c) a battery disposed within the device housing and operatively connected to the capacitor, the battery comprising an electrode assembly, and an electrolyte (d) a hermetically sealed battery housing within which the electrode assembly and the electrolyte are disposed, the housing comprising a cover, a shallow case having a (preferably) planar bottom, an open top to receive the cover; and at least two sides being radiused at intersections with the bottom wherein the radiused sides of the battery case nests within one of the arcuate edges of the device housing, (e) a headspace region extending from a portion of one side, and (f) a feedthrough assembly providing electrical communication between at least one electrode and implantable medical device circuitry.

Methods of manufacturing batteries for implantable medical devices according to the present invention may include one or more of the following steps: (a) providing a shallow battery case having an open end, a base located opposite the open end, and a plurality of sides being radiused at intersections with each other and the base, (b) inserting an electrode assembly into the battery case, (c) placing a cover over the open end of the case, and hermetically sealing the cover to the case, and (d) placing an electrolyte inside the battery case.

BRIEF DESCRIPTION OF THE DRAWINGS

FIG. 1 is an exploded perspective view of a battery according to the present invention;

DETAILED DESCRIPTION OF THE PREFERRED EMBODIMENTS

Figure 2:
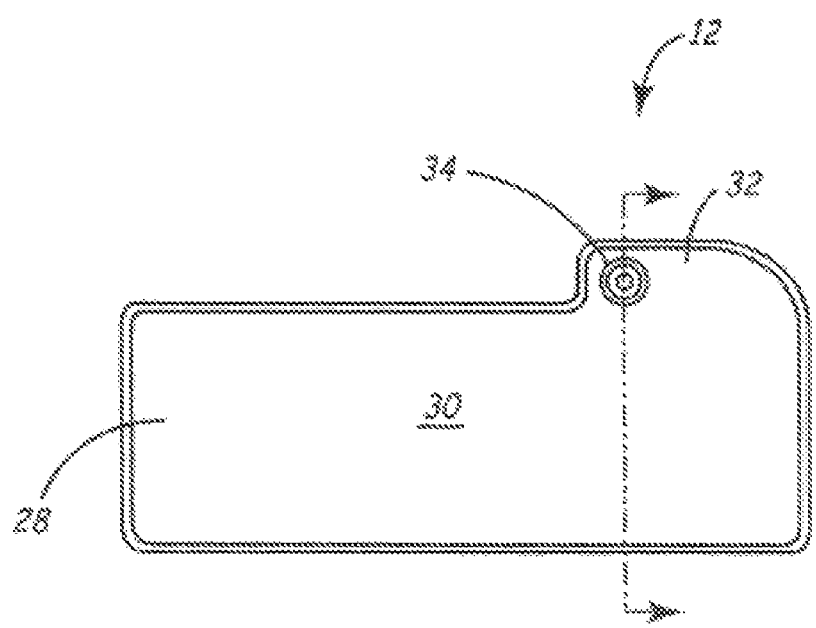
FIG. 2 is a bottom profile of a battery case embodiment of the present invention.

The following detailed description is to be read with reference to the drawings, in which like elements in different drawings have like reference numerals. The drawings, which are not necessarily to scale, depict selected embodiments and are not intended to limit the scope of the invention. Skilled artisans will recognize that the examples provided herein have many useful alternatives that fall within the scope of the claimed invention.

The present invention is not limited to implantable cardioverter defibrillators and may be employed in many various types of electronic and mechanical devices for treating patient medical conditions such as pacemakers, defibrillators, neurostimulators, and therapeutic substance delivery pumps. It is to be further understood; moreover, the present invention is not limited to high current batteries and may utilized for low or medium current batteries. For purposes of illustration only, however, the present invention is below described in the context of high current batteries.

As used herein, the term battery (or batteries) include a single electrochemical cell or cells. Batteries are volumetrically constrained systems in which the components in the case of the battery cannot exceed the available volume of the battery case. Furthermore, the relative amounts of some of the components can be important to provide the desired amount of energy at the desired discharge rates. A discussion of the various considerations in designing the electrodes and the desired volume of electrolyte needed to accompany them in, for example, a lithium/silver vanadium oxide (Li/SVO) battery is discussed in U.S. Pat. No. 5,458,997 (Crespi et al.). Generally, however, the battery must include the electrodes and additional volume for the electrolyte required to provide a functioning battery.

The present invention is particularly directed to high current batteries that at least with respect to ICDs are capable of charging capacitors with the desired amount of energy, preferably about 20 joules or more, typically about 20 joules to about 40 joules, in the desired amount of time, preferably about 20 seconds or less, more preferably about 10 seconds or less. These values can typically be attained during the useful life of the battery as well as when the battery is new. As a result, the batteries must typically deliver up to about 5 amps at about 1.5 to about 2.5 volts, in contrast to low rate batteries that are typically discharged at much lower currents. Furthermore, the preferred batteries must be able to provide these amounts of energy repeatedly, separated by about 30 seconds or less, more preferably by about 10 seconds or less.

With reference to FIG. 1, a preferred battery according to the present invention is depicted. Battery 10 is comprised of a battery case 12 (FIG. 2), electrode assembly 14, insulator cup 16, battery cover 18, coupling 20, headspace cover 22, feedthrough assembly 24, and battery case liner 31. The battery case 12 is designed to enclose the electrode assembly 14 and be hermetically sealed with battery cover 18.

Figure 3:
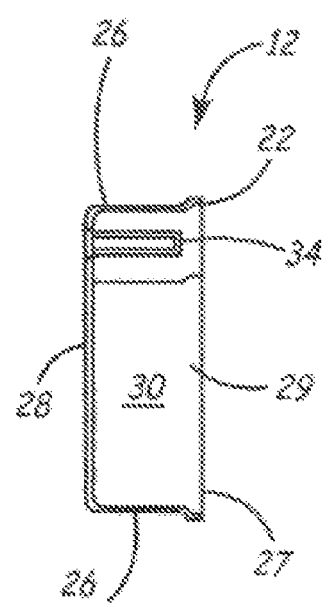
FIG. 3 is a side profile battery case embodiment of the present invention.

With reference to FIGS. 2 & 3, a bottom and side profile respectively is shown of a battery case. Battery case 12 is comprised of battery space 30 which houses electrode assembly 14, headspace 32, fillport 34, which allows for the input of electrolyte into battery 10, and open end 29. Battery case 12 is preferably generally arcuate in shape where sides 26 meet with top 28 of battery case 12. This construction provides a number of advantages including the ability to accommodate the curved or arcuate ends of a preferred coiled electrode assembly 14. As will be more fully discussed below, the arcuate sides 26 can also nest within the arcuate edges of an implantable medical device such as an implantable cardiac defibrillator.

Battery case 12 is preferably made of a medical grade titanium, however, it is contemplated that battery case 12 could be made of almost any type of material, such as aluminum and stainless steel, as long as the material is compatible with the battery's chemistry in order to prevent corrosion. Further, it is contemplated that shallow battery case 12 could be manufactured from most any process including but not limited to machining, casting, stamping, milling, so-called rapid prototyping techniques (e.g., using an SLA and the like) thermoforming, injection molding, vacuum molding, etc., however, case 12 is preferably manufactured using a shallow drawing process. Headspace 32 houses insulators and connector tabs, which transfer electrical energy from electrode assembly 14 to the implantable medical device circuitry and will be discussed in more detail below. However, as shown in FIG. 2, a significant amount of headspace is reduced from prior battery assemblies such as the one shown in FIG. 13.

With reference again to FIG. 3, lip 27 is utilized to hold battery cover 18 in place not allowing cover 18 to drop within battery case 12. Further, lip 27 provides protection to electrode assembly 14 during the welding process, which is preferably performed by laser welding, however, other methods of attachment are contemplated. For example, resistance welding, brazing, soldering and similar techniques may be employed and/or adhesive materials may be used to couple the cover 18 to the case 12. Lip 27 provides a shelf or ledge designed to reduce the likelihood of, if not completely prevent, a portion of radiation emitted from the laser beam from penetrating battery case 12 and damaging radiation sensitive components therein. This would be especially true if this shelf were not present and a gap between cover 18 and case 12 were present there would exist a large risk that electrode assembly 14 could be damaged by a laser penetrating the gap and causing heat damage to electrode assembly 14.

Figure 4:
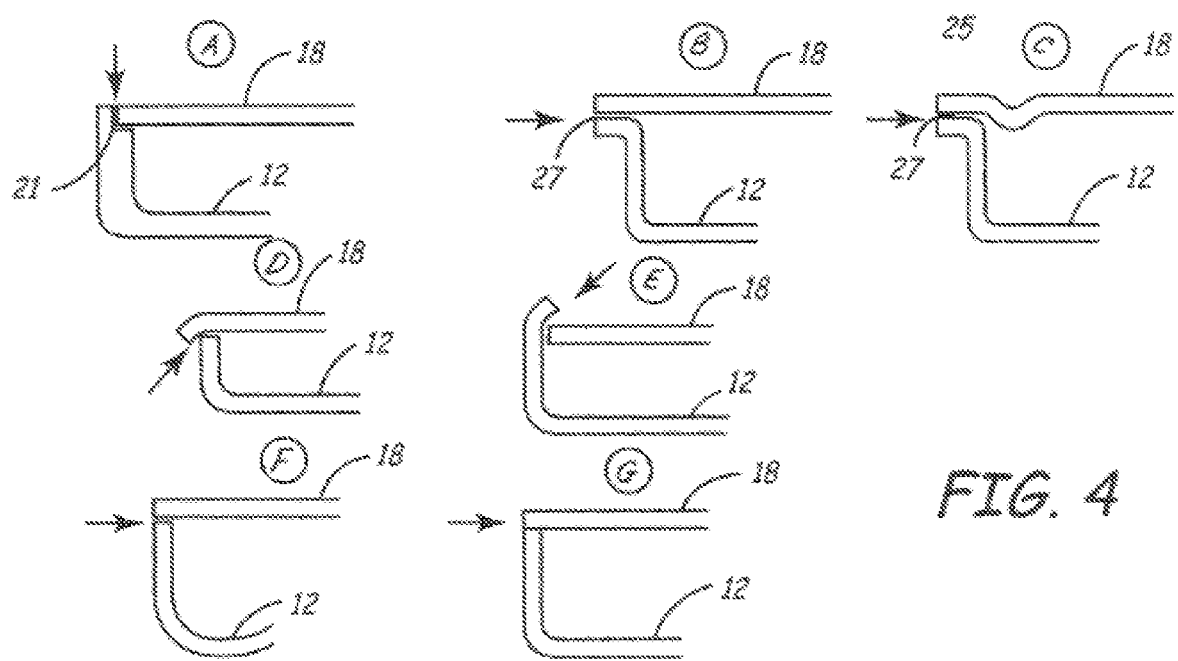
FIG. 4 is cutaway side profile of several attachment embodiments between a battery cover and a battery case.

With reference to FIG. 4, several cutaway side profiles of attachment embodiments between a battery cover and a battery case are shown. In profile A, lip 27 is cut at 90° to provide even more protection during the welding process. While more protection is typically desired, the 90° lip 27 of profile A can be difficult to manufacture. In profile B, lip 27 is bent outward and then preferably cover 18 is placed overtop and butt welded to case 12. In profile C, lip 27 is also bent outward, however, in profile C, a crimp 25 is utilized to help prevent a laser beam from penetrating battery case 12. In profile D, lip 27 is eliminated and the outer edge of cover 18 is bent over before being welded to case 12 to help prevent the laser from penetrating case 12 during welding. In profile E, the outer edge of case 12 is bent over top of cover 18 before being welded. In profile F, cover 18 simple rests upon the upper edge of case 12 and then is butt welded together. In profile G, the upper edge of case 12 is bent slightly inward with cover 18 resting upon to be butt welded to case 12. Each of these embodiments is meant to provide protection to electrode assembly 14 during the welding process, which is preferably performed by laser welding, however, other methods of attachment are contemplated. Each embodiment is meant to prevent the welding laser beam (represented by the arrow in the Figure) from penetrating battery case 12 and damaging electrode assembly 14. Further, the term welding can encompass many types of attachment such as resistance welding and brazing, however, all welds are preferably laser welds. It is also contemplated that many types of attachment could be utilized without departing from the spirit of the invention.

As discussed above, traditional battery cases were deep cases wherein the opening to the case was perpendicular to the deepest portion of the battery. There are two major drawbacks to this traditional design. First, there are manufacturing limitations to the amount of curvature, which can be implemented into the case. Therefore, most cases would have a substantially prismatic case, which, as discussed above, is very limiting when packaging the case within the implantable medical device. Second, because the headspace exists at the open end of the case, it consumes an entire side of the case. In contrast to deep cases, battery case 12 is manufactured using a shallow form process, which allows for corners of case 12 to be radiused as well as providing for the possibility of many varying shapes of case 12. By doing so, the volume case 12 occupies is substantially reduced. Further, because battery case 12 can be manufactured with various shapes and contours, a substantial amount of headspace room can be eliminated and thus more volume within the implantable medical device can be reduced. The inventors of the present invention have found a reduction in excess of on the order of about 10%.

Figure 5:
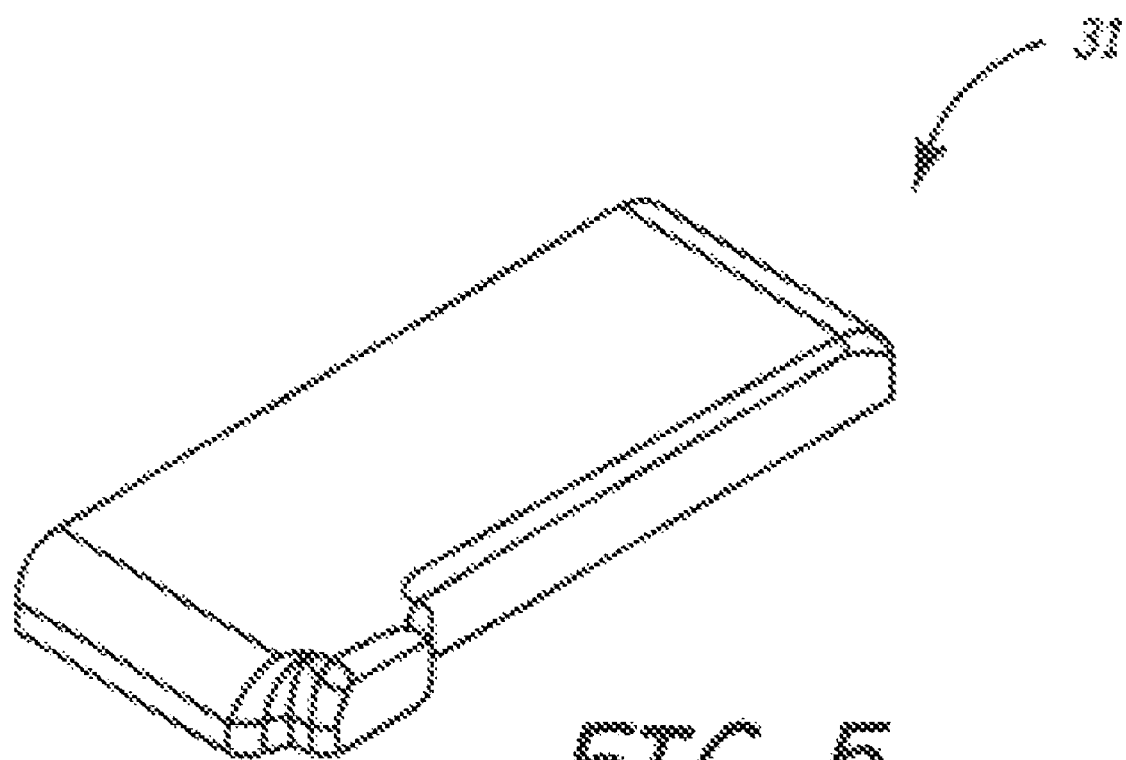
FIG. 5 is a side elevated perspective of a battery case liner of the present invention.

With reference to FIG. 5, a battery case liner used to isolate the battery case from the electrode assembly is shown. Case liner 31 is preferably comprised of ETFE and has a thickness of 0.013 cm. (0.004 inches), however, other thicknesses and types of materials are contemplated such as polypropylene, silicone rubber, polyurethane, fluoropolymers, and the like. Case liner 31 preferably has substantially similar dimensions to battery case 12 except that case liner 31 would have slightly smaller dimensions so that it can rest inside of battery case 12. From the case liner's shape as shown in FIG. 5 and the battery case's shape as shown in FIG. 2, it is clear to one of skill in the art how case liner 31 would rest within battery case 12. For example, the headspace area of case liner 31 would line up with headspace 32 of battery case 12 except it would be slightly smaller to accommodate for fillport 34.

Figure 6:
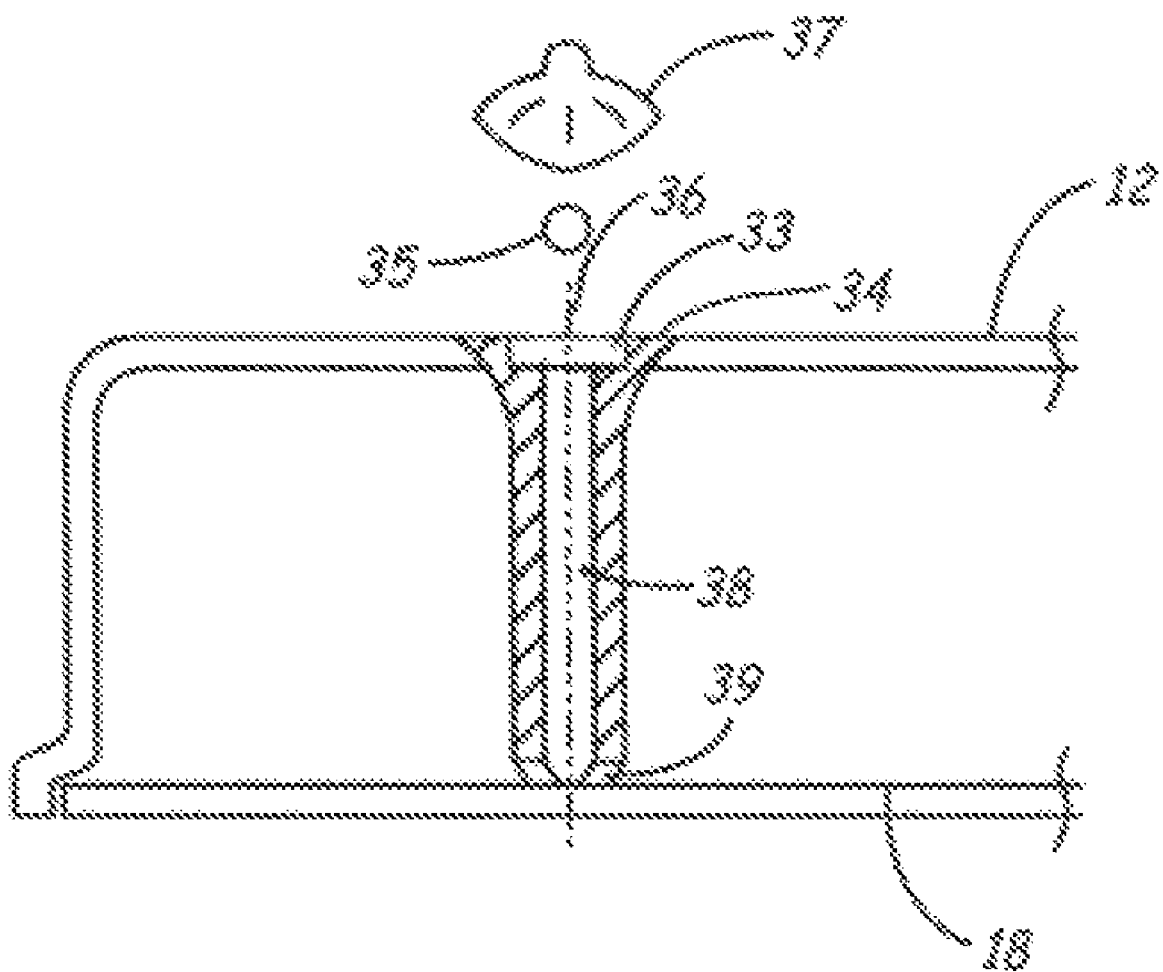
FIG. 6 is a front profile of an electrolyte fillport embodiment of the present invention.

With reference to FIG. 6, a front profile of the electrolyte fillport is shown with a fillport ball seal and a closing button. Fillport 34 is used to route lithium hexafluoroarsenate electrolyte into battery 10. Although lithium hexafluoroarsenate is preferably used for the present embodiment, it is contemplated that most any chemical electrolyte could be used without departing from the spirit of the invention. Fillport 34 is preferably laser welded to battery case 12 and preferably has a hermetic seal to ensure no electrolyte leakage. However, it is contemplated that fillport 34 could be attached to case 12 in any fashion, such as any suitable hermetic joint as is known to those of skill in the art. Fillport 34 is preferably comprised of titanium and has a diameter of 0.1117 inches at the top and 0.060 inches at the bottom, however, it is fully contemplated that fillport 34 could be most any thickness or type of electrochemically compatible material. However, for the ease of manufacturing and reliability of the weld, case 12 and fillport 34 are preferably made from the same material.

From the figure it is shown that fillport 34 has an opening 36 in which to receive an electrolyte injection device that transfers electrolyte from the device to battery 10 through conduit 38. Further, it is shown that the upper portion of fillport 34 is tapered so that fillport 34 can rest within an opening in case 12 before fillport 34 is welded to case 12. It is of note that the opening in case 12 for fillport 34 does not necessarily have to be located in headspace 32 and can be located anywhere in case 12 or cover 18 without departing from the spirit of the invention. Once the electrolyte has been injected within battery 10, fillport ball seal 35 is placed within conduit 38 to create a "press-fit" hermetic seal, which prevents any electrolyte from escaping through conduit 38. Closing button 37 is then placed over aperture 33 and is welded to fillport 34. Closing button 37 is preferably comprised of medical grade titanium and ball seal 35 is preferably comprised of a titanium alloy of titanium aluminum and vanadium, however, other materials and alloys are contemplated as long as they are electrochemically compatible. It is further shown in the figure that fillport 34 is tapered from the top to the bottom. This provides for maximum space inside battery 10, further the taper provides a larger upper area for button 37 to be welded to, which allows for button 37 to be larger and thus easier to handle and weld to fillport 34.

With further reference to FIG. 6, it is shown that fillport 34 extends entirely from case 12 to cover 18. Since case 12 and cover 18 are preferably 0.038 cm. (0.015 inches) thick, fillport 34 provides support by extending from case 12 to cover 18 so that an indentation or denting does not occur during the "press-fit" operation where ball seal 35 is pressed within conduit 38. If fillport 34 did not extend from case 12 to cover 18 there is a risk that denting could occur during the "press-fit" operation due to the thinness of case 12 and cover 18. Further, distal end 39 of fillport 34 is tapered so that electrolyte can freely enter battery 10. The taper allows conduit 38 to be unobstructed by cover 18 and thus the injection of electrolyte occurs more easily.

Other fillport embodiments and locations are contemplated without departing from the spirit of the invention. One embodiment includes a low profile fillport (e.g., one that does not extend from the case to the cover) that is located near the corners of case 12 and cover 18. In this embodiment, indentation during the "press-fit" is inhibited by the support provided by the sides of case 12 (or cover 18) in the corner. Further, this embodiment can be implemented in case 12 or cover 18 as long as the low profile fillport is placed in a corner of the vessel defined by case 12 and cover 18 of the battery 10. In another fillport embodiment, a filltube is located on case 12 or cover 18. After the electrolyte is injected into battery 10, the filltube is crimped shut and welded. This embodiment eliminates the "press-fit" operation. In another embodiment, a plug or button is welded over or into an open port where the electrolyte is injected. This embodiment eliminates a redundant seal. In yet another embodiment, a gasket seal or epoxy is utilized to plug an open port.

Figure 7:
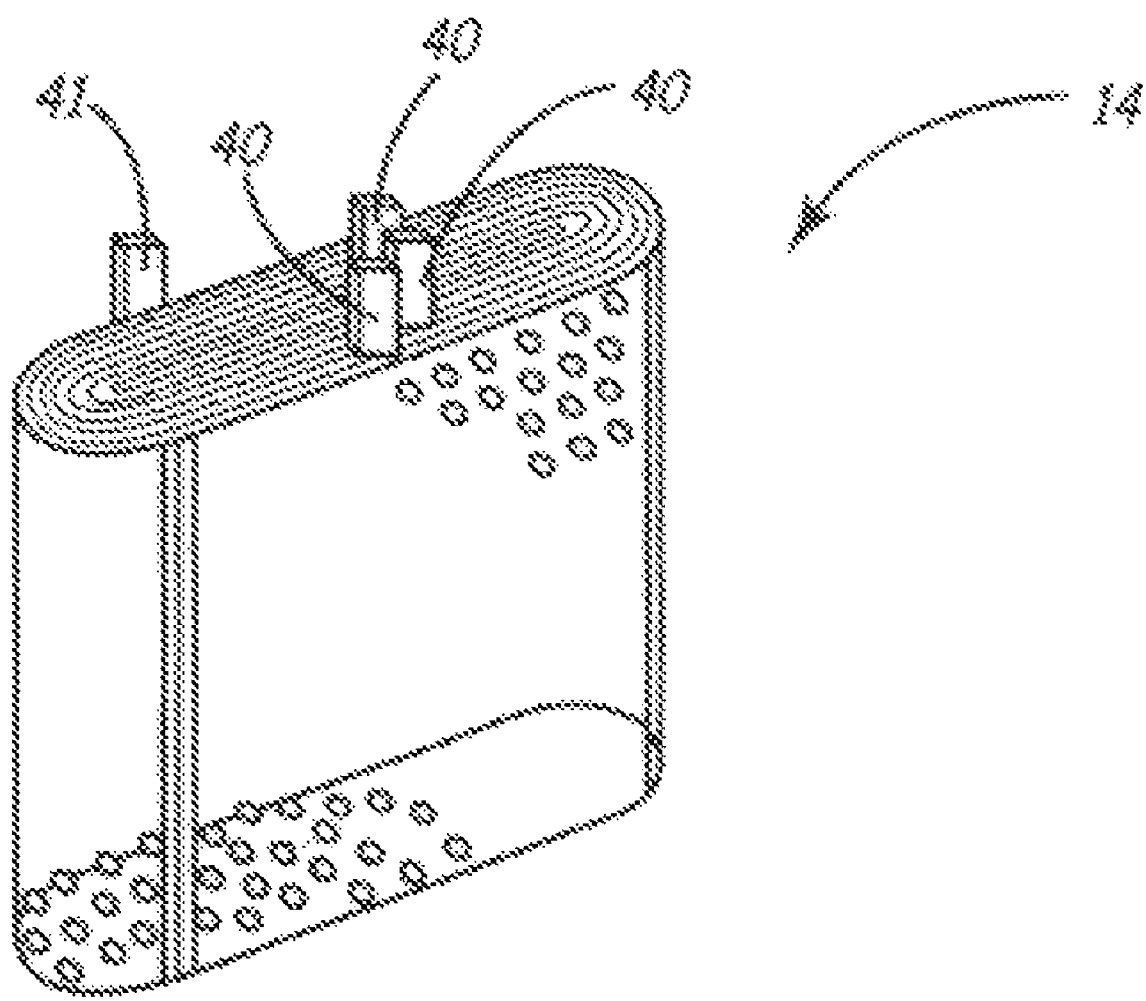
FIG. 7 is a side elevated perspective of an electrode assembly embodiment of the present invention.

With reference to FIG. 7, the details regarding construction of electrode assembly 14, such as connector tabs, electrode pouches, etc., are secondary to the present invention and will be described generally below with a more complete discussion being found in, e.g., U.S. Pat. No. 5,458,997 (Crespi et al.). With reference to FIG. 7, electrode assembly 14 is preferably a wound or coiled structure similar to those disclosed in, e.g., U.S. Pat. No. 5,486,215 (Kelm et al.) and U.S. Pat. No. 5,549,717 (Takeuchi et al.). However, electrode assembly 14 could be a folded or stacked electrode assembly structure. The composition of the electrode assemblies can vary, although one preferred electrode assembly includes a wound core of lithium/CSVO. Other battery chemistries are also anticipated, such as those described in U.S. Pat. No. 5,616,429 to Klementowski and U.S. Pat. No. 5,458,997 to Crespi et al., with the preferred cores comprising wound electrodes. Such a design provides a volumetrically efficient battery useful in many different implantable devices.

Electrode assembly 14 preferably includes an anode, a cathode, cathode connector tabs 40, anode connector tab 41, and a porous, electrically non-conductive separator material encapsulating either or both of the anode and cathode. These three components are wound to form electrode assembly 14. The anode portion of the electrode assembly can comprise a number of different materials including an anode active material located on an anode conductor element. Examples of suitable anode active materials include, but are not limited to: alkali metals, materials selected from Group IA of the Periodic Table of Elements, including lithium, sodium, potassium, etc., and their alloys and intermetallic compounds including, e.g., Li—Si, Li—B, and Li—Si—B alloys and intermetallic compounds, insertion or intercalation materials such as carbon, or tin-oxide. Examples of suitable materials for the anode conductor element include, but are not limited to: stainless steel, nickel, titanium, or aluminum. However, in a preferred embodiment the anode is comprised of lithium with a titanium conductor.

The cathode portion of the electrode assembly preferably includes a cathode active material located on a cathode current collector that also conducts the flow of electrons between the cathode active material and the cathode terminals of electrode assembly 14. Examples of materials suitable for use as the cathode active material include, but are not limited to: a metal oxide, a mixed metal oxide, a metal sulfide or carbonaceous compounds, and combinations thereof. Suitable cathode active materials include silver vanadium oxide (SVO), copper vanadium oxide, combination silver vanadium oxide (CSVO), manganese dioxide, titanium disulfide, copper oxide, copper sulfide, iron sulfide, iron disulfide, carbon and fluorinated carbon, and mixtures thereof, including lithiated oxides of metals such as manganese, cobalt, and nickel. However, in a preferred embodiment the cathode is comprised of CSVO with a titanium conductor.

Preferably, the cathode active material comprises a mixed metal oxide formed by chemical addition, reaction or otherwise intimate contact or by thermal spray coating process of various metal sulfides, metal oxides or metal oxide/elemental metal combinations. The materials thereby produced contain metals and oxides of Groups IB, IIB, IIIB, IVB, VB, VIB, VIIB, and VIII of the Periodic Table of Elements, which includes noble metals and/or their oxide compounds.

The cathode active materials can be provided in a binder material such as a fluoro-resin powder, preferably polytetrafluoroethylene (PTFE) powder that also includes another electrically conductive material such as graphite powder, acetylene black powder, and carbon black powder. In some cases, however, no binder or other conductive material is required for the cathode.

The separator material should electrically insulate the anode from the cathode. The material is preferably wettable by the cell electrolyte, sufficiently porous to allow the electrolyte to flow through the separator material, and maintain physical and chemical integrity within the cell during operation. Examples of suitable separator materials include, but are not limited to: polyethylenetetrafluoroethylene, ceramics, non-woven glass, glass fiber material, polypropylene, and polyethylene.

Figure 8:
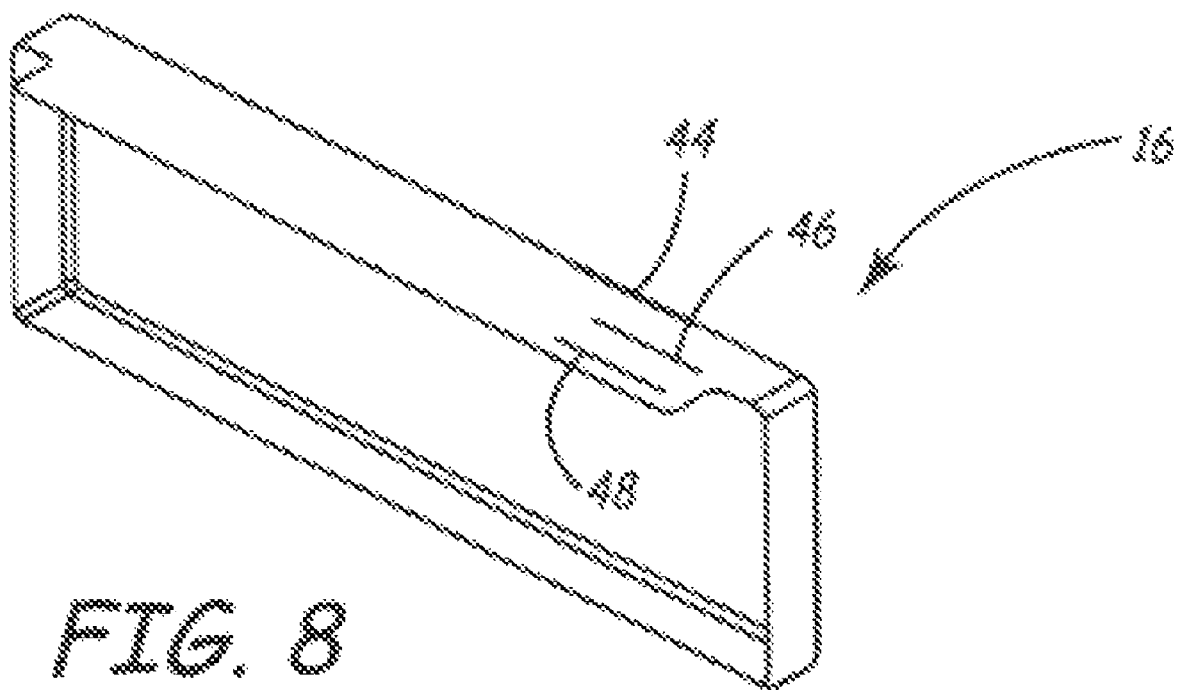
FIG. 8 is a side elevated perspective of an insulator cup embodiment of the present invention.

As best seen in FIG. 1, an insulator cup 16 is used to electrically isolate electrode assembly 14 from battery cover 18. With reference to FIG. 8, an insulator cup embodiment of the present invention is shown. Insulator cup 16 includes slits 44, 46, and 48 to accommodate connector tabs 40 and anode tab 41. Preferably insulator cup 16 is comprised of ETFE with a thickness of 0.030 cm. (0.012 inches), however, it is contemplated that other thicknesses and materials could be used such as high density polyethylene (HDPE), polypropylene, polyurethane, fluoropolymers, and the like. Insulator cup 16 performs several functions including working in conjunction with battery case liner 31 to isolate battery case 12 and battery cover 18 from electrode assembly 14. It also provides mechanical stability for electrode assembly 14. In addition, it serves to hold the coil assembly together which substantially aids in the manufacturing of battery 10. Since electrode assembly 14 is preferably a wound coil, insulator cup 16 also helps prevent assembly 14 from unwinding. Insulator cup 16 further provides protection for assembly 14 during handling and during the life of assembly 14. Finally, and most importantly cup 16 provides a thermal barrier between assembly 14 and cover 18 during the laser welding procedure that joins cover 18 with case 12, which is discussed in more detail below.

As stated above in detail, case 12 and cover 18 are preferably welded together to provide a hermetic enclosure for electrode assembly 14. However, because of the battery's structure, the weld is performed within 1 mm of electrode assembly 14. Since, case 12 and cover 18 are first assembled before the welding process, a finite gap between case 12 and cover 18 typically exists. However, any time there is a finite gap there is the possibility that the laser beam utilized in the laser welding process may penetrate battery 10 and damage electrode assembly 14. Therefore, molded insulator cup 16 is preferably comprised of ETFE and further is preferably compounded or mixed with carbon black, although cup 16 may be simply coated with carbon black in lieu of the foregoing. The carbon coloring serves to make the insulator black. The black color serves to shield electrode assembly 14 from laser beam penetration into battery 10. Essentially cup 16 is opaque to the laser wavelength, which is approximately 1 micron. Alternatively, this thermal protection could be accomplished with a metal ring compatible with case 12 and cover 18, such as titanium, stainless steel, niobium, etc., however, preferably cup 16 is an opaque polymer as discussed above.

Figure 10:
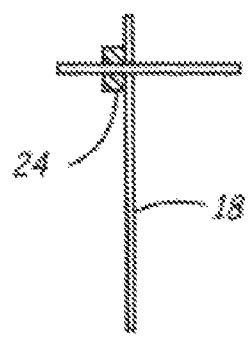
FIG. 10 is a side profile of a battery cover with a header assembly of the present invention.
Figure 9:
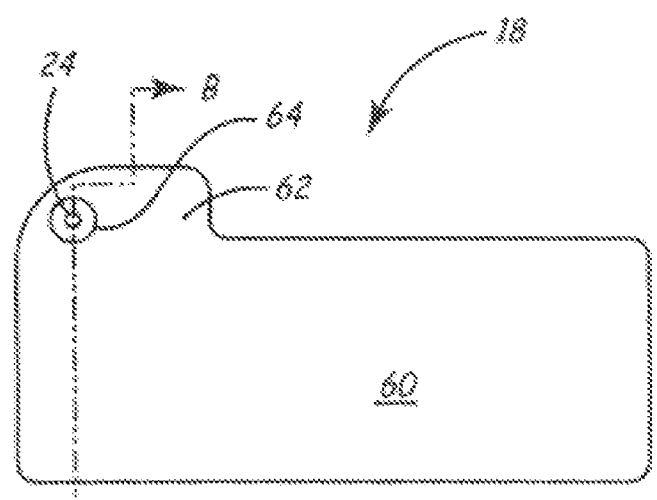
FIG. 9 is a top profile of a battery cover with a header assembly of the present invention.

With reference to FIGS. 9 and 10, a top and side profile of a battery cover with a feedthrough assembly is shown. Battery cover 18 is comprised of an electrode assembly region 60, a headspace region 62, and a feedthrough aperture 64. Similar to battery case 12, battery cover 18 is comprised of medical grade titanium to provide a strong and reliable weld creating a hermetic seal with the battery case. However, it is contemplated that battery cover 18 could be made of any type of material as long as the material was electrochemically compatible. Battery cover 18 is designed to fit overtop the shallow opening 29 within lip 27 on the perimeter of opening 29. Therefore battery cover 18 rests on the small lip, substantially flush with the top of opening 29 which provides for substantial ease of manufacturing when battery cover 18 is laser welded to battery case 12.

Figure 11:
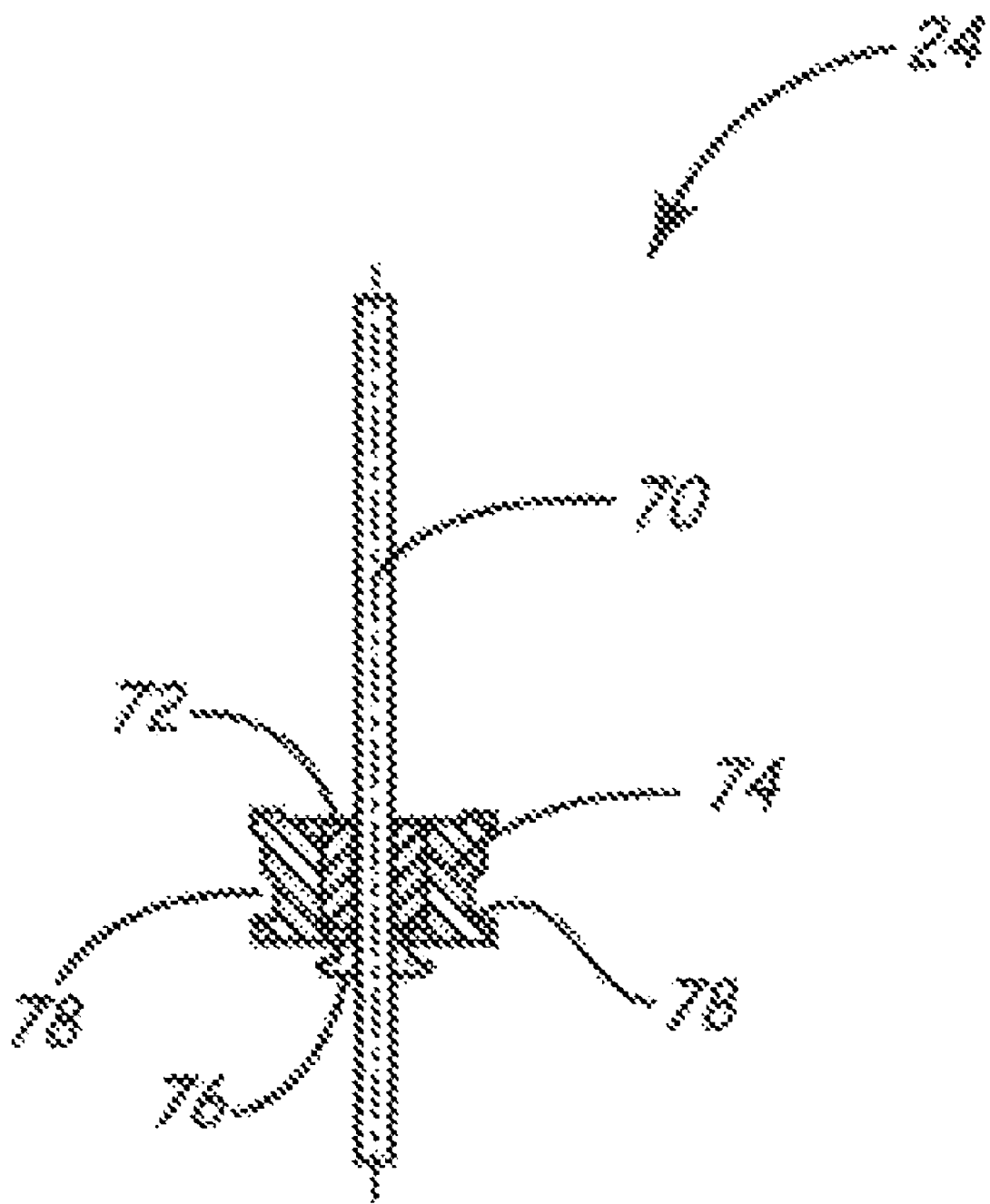
FIG. 11 is a front profile embodiment of a feedthrough assembly of the present invention.

Feedthrough aperture 64 is tapered outwardly not only to allow feedthrough assembly 24 to rest within aperture 64, but also to provide an isolation buffer between glass member 72 and the weld which will attach feedthrough assembly 24 to battery cover 18. With reference to FIG. 11, an embodiment for the feedthrough assembly is shown. Feedthrough assembly 24 is comprised of feedthrough pin 70, glass sealing member 72, ferrule 74, flange 76, and retention slots 78. As is shown in the figure, ferrule 74 is tapered at a substantially equal angle as the tapers on feedthrough aperture 64 so that it may be received within aperture 64. This tapered portion of ferrule 74 is also the location where the weld to join feedthrough assembly 24 to battery cover 18 occurs. The taper of ferrule 74 not only places the weld further from glass member 72, but also creates more surface area in which to dissipate the heat from the weld. As is discussed above, feedthrough aperture 64 and assembly 24 can be located anywhere on case 12 or cover 18.

Feedthrough pin 70 is preferably comprised of niobium, however, any conductive material could be utilized without departing from the spirit of the invention. Niobium is preferably chosen for its low resistivity, its material compatibility during welding with titanium, and its coefficient of expansion when heated. As will be discussed in more detail below, pin 70 is preferably welded to coupling 20 (FIG. 12) and to connector module 100 (FIG. 17) located outside of battery 10. Coupling 20 and contacts 114 and 116 on connector module 100 are preferably made of niobium and titanium respectively. Niobium and titanium are compatible metals, meaning that when they are welded together a strong reliable weld is created. Pin 70 has a diameter of 0.055 cm. (0.0216 inches), preferably selected for a high current application. Glass sealing member 72 is comprised of CABAL-12 (calcium-boroaluminate) glass, which provides electrical isolation of feedthrough pin 70 from battery cover 18. The pin material is in part selected for its suitability in feedthrough assembly 24 for its ability to join with glass sealing member 72, which results in a hermetic seal.

CABAL-12 is very corrosion resistant as well as being a good insulator. Therefore, CABAL-12 provides for good insulation between pin 70 and battery cover 18 as well as being resistant to the corrosive effects of the electrolyte. Preferably glass member 72 provides an electrical insulation resistance of 1000 M-ohms from pin 70 to ferrule 74 at 100 VDC per Mil-STD 202F method 302. Glass member 72 is then preferably placed within a conduit on ferrule 74 having a diameter of 0.060 inches. Preferably glass member 72 provides a hermetic seal both with pin 70 and ferrule 74 having a leak rate not exceeding $10^{-8}$ ATM STD cc/sec of helium per MIL-STD 202F method 112E. Ferrule 74 is preferably comprised of medical grade titanium that is annealed according to ASTM F67. Although, preferable materials have been listed for the components listed above, it is contemplated that other materials could be utilized. Feedthrough pin 70, sealing member 72, and ferrule 74 are heated together to allow the glass to melt and reform to seal within ferrule 74 and around pin 70.

After pin 70, glass member 72, and ferrule 74 are placed together; the bottom of ferrule 74 is subjected to an overmolding process where it is coated with polypropylene to provide electrical insulation between pin 70 and ferrule 74. The polypropylene overmold helps prevent pin 70 from being bent over to touch ferrule 74 thus creating an electrical short. The overmolding also provides mechanical short protection for other situations, such as pin 70 bending to bridge to connector tabs 40 and 41. Further, the polypropylene coating limits the amount of electrolyte exposure to glass member 72. It is contemplated that other insulation materials could be used as a coating such as PETFE (polyethylene tetra fluoro ethylene), ETFE (ethylene tetrafluorethylene), polyurethane, polyethylene, and the like. The polypropylene molding is held in place by retention slots 78, which act to prevent the molding from twisting off or pulling away from feedthrough assembly 24. Further, during the overmolding process flange 76 is created. Flange 76 provides a retention means for headspace insulator 22 (FIG. 14), which is discussed in more detail below. Preferably flange 76 has a thick plastic-thin plastic-thick plastic design, which allows for insulator 22 to be snapped onto flange 22.

In another embodiment, the overmolding is extended out over a plate with slots for cathode tabs 40. Tabs 40 are then welded to the plate, which in turn is welded to feedthrough pin 70. This embodiment provides a relatively rigid system, which has advantages of preventing insulators from inadvertently folding or collapsing out of place.

Figure 12:
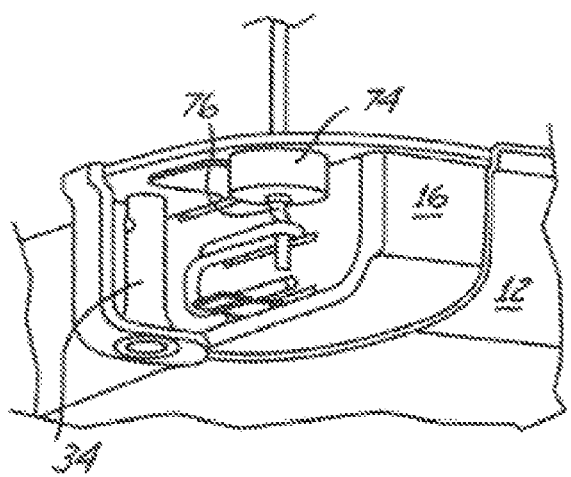
FIG. 12 is a cutaway view of a headspace embodiment showing the feedthrough pin connection with the coupling.

With reference to FIG. 12, an embodiment showing the interconnection between a feedthrough pin and a coupling is shown. As is shown, coupling 20 is welded to cathode tabs 40 while anode tab 41 is in contact with battery cover 18. Coupling 20 is preferably comprised of niobium with a diameter of 0.055 cm. (0.0216 inches), which is compatible with pin 70. Coupling 20 is welded to feedthrough pin 70 to provide an electrical connection between the cathode of electrode assembly 14 and the implantable medical device. While for the purposes of this discussion coupling 20 is welded to cathode tabs 40 and feedthrough pin 70, it is contemplated that an alternate method of attachment may be utilized such as soldering, electrically conductive glue, or an electrically conductive thermoset material and the like, without departing from the spirit of the invention. At the time of the present invention, however, the inventors have found that welding provides the most reliable connection. Coupling 20 allows for ease in manufacturing by eliminating the need to bend tabs 40 or pin 70 to reach a coupling between them. Since coupling 20 has a "U" shape it allows for more compliance in aligning with the position of tabs 40 and pin 70.

Figure 13:
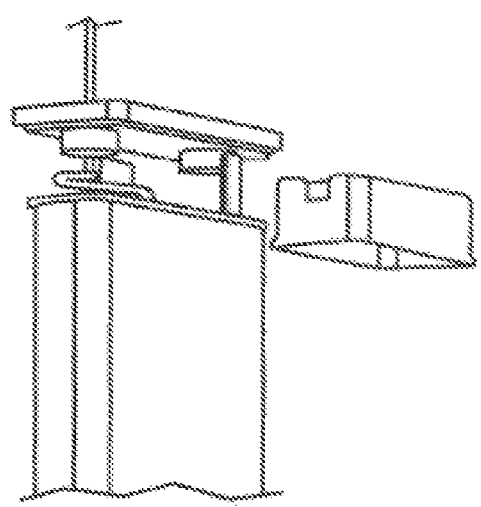
FIG. 13 is an elevational, exploded pictorial view of the headspace in prior art implantable medical device batteries.

What is further shown with reference to FIG. 12 is that the headspace volume is substantially reduced when compared with prior implantable medical device batteries as shown in FIG. 13 and as discussed above.

Figure 14:
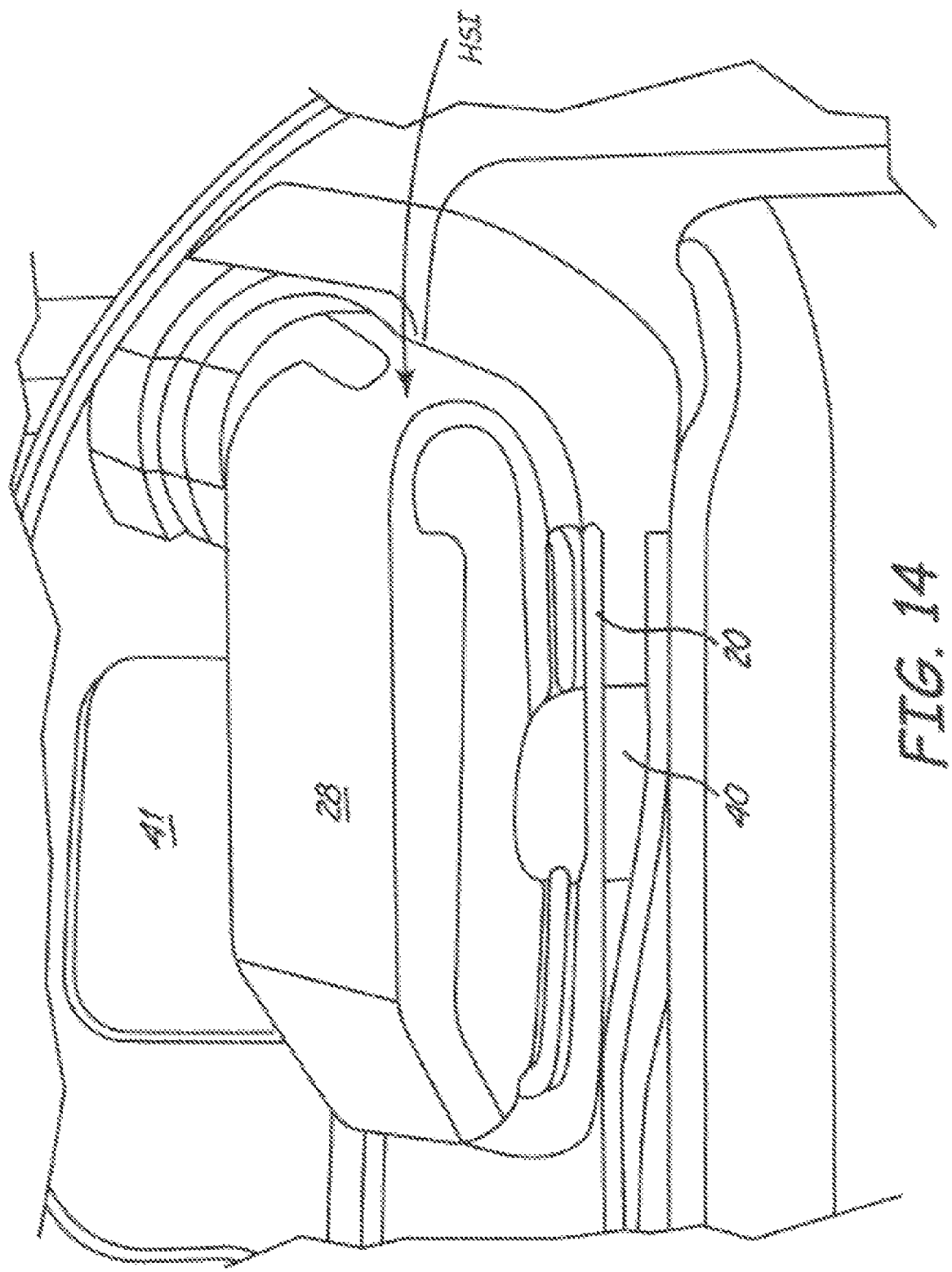
FIG. 14 is an elevated perspective of a headspace insulator embodiment of the present invention.
Figure 15:
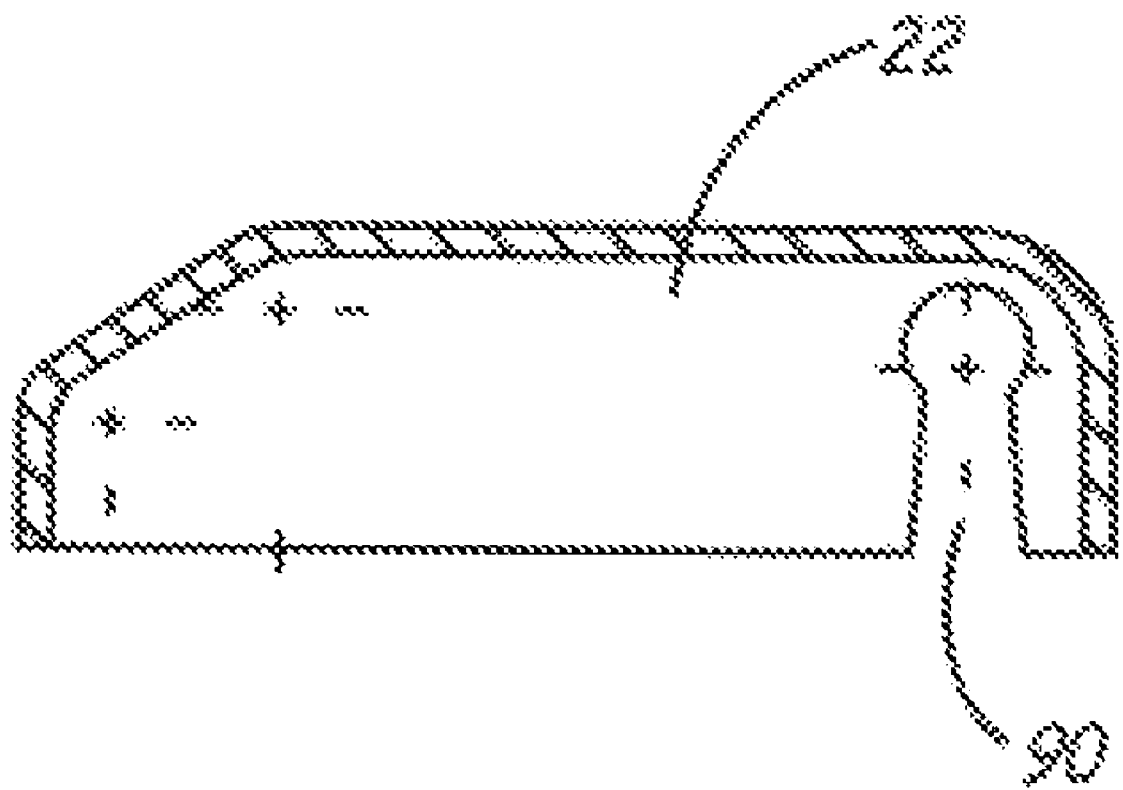
FIG. 15 is a rear profile perspective of a headspace insulator embodiment of the present invention.

With respect to FIG. 14, a headspace insulator is shown. Preferably headspace insulator 22 is comprised of polypropylene, however, other insulative materials are contemplated. Headspace insulator 22 preferably covers coupling 20 and cathode tabs 40. Insulator 22 is designed to provide mechanical line of sight insulation and electrical protection from electrical shorts. Insulator 22 also prevents any materials from contacting cathode tabs 40 and coupling 20, which could compromise the battery's operation. With reference to FIG. 15, which shows a rear profile view of the headspace insulation, slot 90 is shown, which snaps onto flange 76 of feedthrough assembly 24. This connection holds insulator 22 into place and protects cathode tabs 40 and coupling 20 during handling and discharge.

Figure 16:
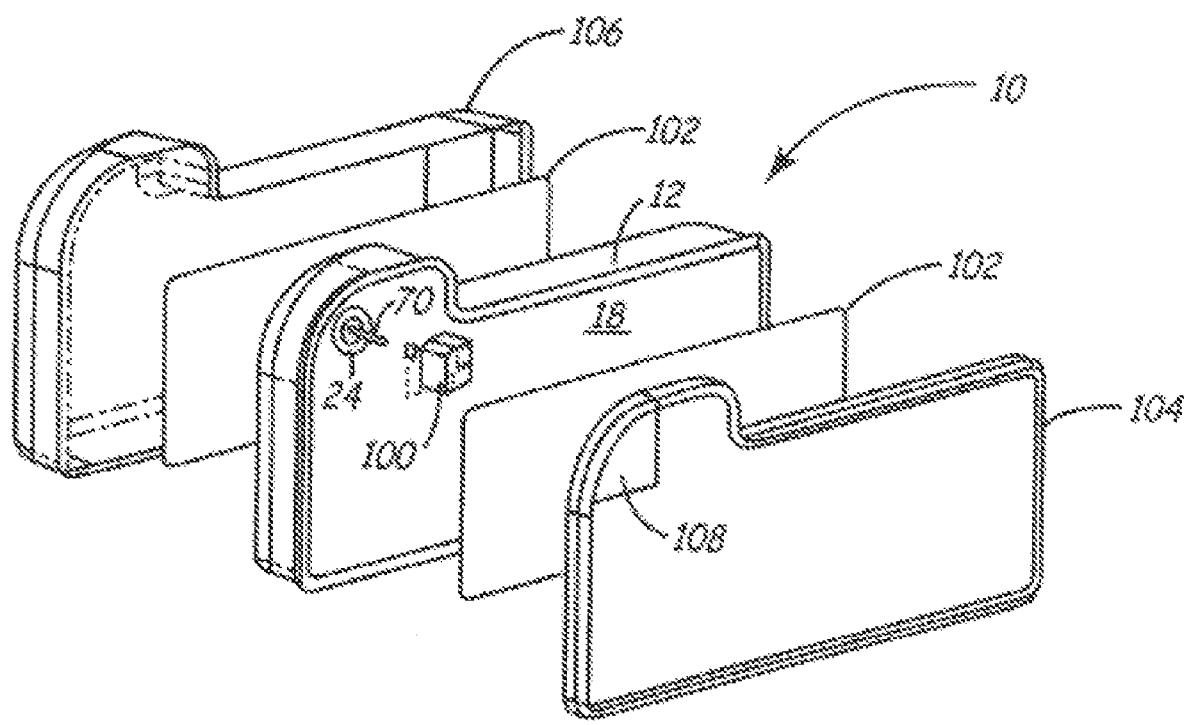
FIG. 16 is an exploded perspective view of battery insulators and connector.

With reference to FIG. 16, a battery assembly with insulators and a battery connector is shown. Upon battery 10 being mechanically assembled as described in detail above, a battery connector 100 is connected to pin 70, which is described in more detail below. Connector 100 is utilized to route the energy from battery 10 to the implantable medical device. In an implantable cardioverter defibrillator the energy would be transferred to a switching system such as that described in U.S. Pat. No. 5,470,341 (Kuehn et al.). Battery insulators 104 and 106 are held in place on battery 10 with two pressure sensitive acrylic adhesive strips 102. These strips are similar to double back adhesive tape, which is tacky on both sides of the tape. While pressure sensitive acrylic is discussed for purposes of the embodiment, it is fully contemplated that other methods of attachment for insulators 104 and 106 could be utilized without departing from the spirit of the invention.

Insulators 104 and 106 are preferably comprised of a thermoplastic polyimide film, however, other insulator materials are contemplated. Insulators 104 and 106 provide electrical and mechanical insulation for battery 10. Since battery case 12 and cover 18 are negatively charged, they need to be electrically isolated from the rest of the implantable medical device. Further, insulators 104 and 106 provide mechanical insulation by protecting battery 10 during handling and thermal protection when the implantable device shields are welded together, which is outside the scope of the present invention.

Figure 17:
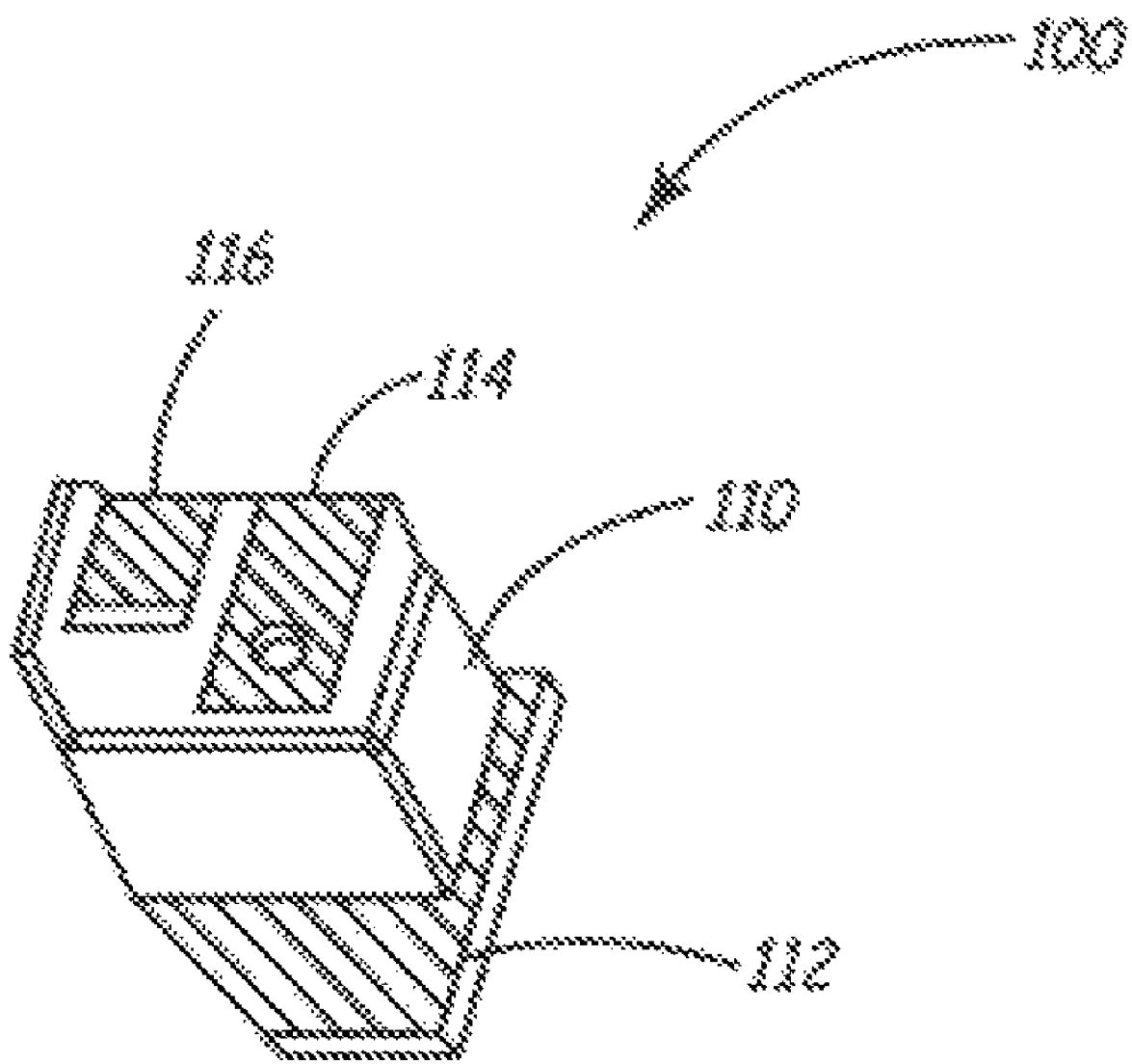
FIG. 17 is an elevated side profile of a battery connector embodiment of the present invention.

With reference to FIG. 17, a battery connector is shown. Connector 100 is comprised of a main body 110, a base 112, a positive contact 114, and a negative contact 116. Main body 110 provides a housing for base 112, positive contact 114, and negative contact 116 and is preferably comprised of polyetherimide, however other insulator materials are contemplated. Body 110 also acts as an insulator to electrically isolate positive contact 114 from negative contact 116. Base 112, positive contact 114, and negative contact 116 are preferably comprised of titanium, however other materials are contemplated. Connector 100 is placed over top of pin 70 in which pin 70 is received by an aperture in positive contact 114. Pin 70 is then preferably laser welded to positive contact 114 as well as base 112 which is laser welded to cover 18. What cannot be shown with reference to FIG. 17 is that negative contact 116 is in contact with base 112. Thus after the laser welding is complete there exists a positive charge on contact 114 and a negative charge on contact 116. Positive contact 114 and negative contact 116 are then ribbon bonded, as is known in the art, to the implantable medical device's circuitry. It is of note that connector 100 is the only exposed portion of battery 10 after it is received through triangular cut 108 as shown in FIG. 15. It is further noted that an alternative embodiment would include a negative charge on contact 114 and a positive charge on contact 116.

It will be appreciated that the present invention can take many forms and embodiments. The true essence and spirit of this invention are defined in the appended claims, and it is not intended that the embodiments of the invention presented herein (i.e., described and/or illustrated) should limit the scope thereof.

What is claimed is:

1. An electrochemical cell comprising an insulator, wherein the electrochemical cell comprises a cell housing joinable to a cell cover, the insulator comprising:
   a case having a bottom, an open top to receive an electrode assembly, and at least one side extending from said bottom; and
   said case being opaque to a laser beam.

2. An electrochemical cell according to claim 1, further comprising slots to receive at least one cathode tab and at least one anode tab.

3. An electrochemical cell according to claim 2, wherein the slots are located on the at least one side.

4. An electrochemical cell according to claim 1, wherein the case bottom is adjacent to the cell cover and provides an electrical barrier between the electrode assembly and the cell cover.

5. An electrochemical cell according to claim 4, wherein the electrode assembly is up to five millimeters from a weld joint joining the cell cover with the cell housing.

6. An electrochemical cell according to claim 5, wherein the case provides a thermal barrier between the weld joint and the electrode assembly.

7. An electrochemical cell according to claim 6, wherein the case provides a radiation barrier between the laser beam and the electrode assembly.

8. An electrochemical cell according to claim 1, wherein the case is comprised of a material selected from the group consisting of HDPE, polypropylene, polyurethane, and fluoropolymers.

9. An electrochemical cell according to claim 1, wherein the case is comprised of ETFE.

10. An electrochemical cell according to claim 9, wherein the case is comprised of ETFE comprising a black resin.

11. An electrochemical cell according to claim 10, wherein the carbon resin provides the laser beam opacity.

12. A battery, comprising:
a electrode assembly including an anode and a cathode;
an electrolyte;
a battery housing enclosing the electrode assembly and within which the electrode assembly and the electrolyte are disposed, the housing comprising a cover, a shallow case having a substantially planar bottom, an open top to receive the cover; and a plurality of sides; and
an insulator having a bottom, an open top to receive the electrode assembly, and at least one side extending from said bottom; said insulator being opaque to a laser beam.

13. A battery according to claim 12, further comprising slots in the insulator to receive at least one cathode tab and at least one anode tab.

14. A battery according to claim 13, wherein the slots in the insulator are located on the at least one side.

15. A battery according to claim 12, wherein the insulator bottom is adjacent to the cover and provides an electrical barrier between the electrode assembly and the cover.

16. A battery according to claim 15, wherein the electrode assembly is up to five millimeters from a weld joint joining the cover with the case.

17. A battery according to claim 16, wherein the insulator provides a thermal barrier between the weld joint and the electrode assembly.

18. A battery according to claim 17, wherein the insulator provides a radiation barrier between the laser beam and the electrode assembly.

19. A battery according to claim 12, wherein the insulator is comprised of a material selected from the group consisting of HDPE, polypropylene, polyurethane, and fluoropolymers.

20. A battery according to claim 12, wherein the insulator is comprised of ETFE.

21. A battery according to claim 20, wherein the insulator is comprised of ETFE comprising a carbon black resin.

22. A battery according to claim 21, wherein the carbon resin provides the laser beam opacity.

23. A method of manufacturing a battery, comprising:
providing a shallow battery case having an open end, a base located opposite the open end, and a plurality of sides being radiused at intersections with each other and the base;
providing an insulator having a bottom, an open top to receive the electrode assembly, and at least one side extending from said bottom; said insulator being opaque to a laser beam;
inserting an electrode assembly into the insulator;
placing a cover over the open end of the case, and hermetically sealing the cover to the case; and
placing an electrolyte inside the battery housing.

24. A method according to claim 23, wherein the insulator is comprised of slots to receive at least one cathode tab and at least one anode tab.

25. A method according to claim 24, wherein the slots in the insulator are located on the at least one side.

26. A method according to claim 23, wherein the insulator bottom is adjacent to the cover and provides an electrical barrier between the electrode assembly and the cover.

27. A method according to claim 26, wherein the electrode assembly is up to 5 mm from a weld joint creating the hermetic seal.

28. A method according to claim 27, wherein the insulator provides a thermal barrier between the weld joint and the electrode assembly.

29. A method according to claim 28, wherein the insulator provides a radiation barrier between a laser beam and the electrode assembly.

* * * * *